United States Patent [19]

Goldbecker et al.

[11] Patent Number: 5,601,650
[45] Date of Patent: Feb. 11, 1997

[54] PROCESS AND DEVICE FOR DYEING HISTOLOGICAL PREPARATIONS ARRANGED ON MICROSCOPE SLIDES

[75] Inventors: Helmut Goldbecker; Reinhard Vauth, both of Isernhagen, Germany

[73] Assignee: Medite Gesellschaft fur Medizintechnik mbH, Burgdorf, Germany

[21] Appl. No.: 150,168

[22] PCT Filed: May 26, 1992

[86] PCT No.: PCT/DE92/00453

§ 371 Date: Jan. 27, 1994

§ 102(e) Date: Jan. 27, 1994

[87] PCT Pub. No.: WO92/21953

PCT Pub. Date: Dec. 10, 1992

[30] Foreign Application Priority Data

May 29, 1991 [DE] Germany ............... 41 17 833.5

[51] Int. Cl.⁶ ............... B05C 11/00; B05C 3/00; B05D 3/00; B05D 1/38
[52] U.S. Cl. ............... 118/697; 118/698; 118/702; 118/425; 427/4; 427/2.11
[58] Field of Search ............... 427/4, 2.11; 118/697, 118/425, 698, 702, 704, 428; 424/3

[56] References Cited

U.S. PATENT DOCUMENTS

| | | | |
|---|---|---|---|
| 3,302,607 | 2/1967 | Kobernick | 118/702 |
| 3,674,040 | 7/1972 | Howells et al. | 134/58 R |
| 3,691,988 | 9/1972 | Clarke | 118/425 |
| 3,771,490 | 11/1973 | Kinney et al. | 118/698 |
| 3,807,353 | 4/1974 | Kobernick | 118/425 |
| 3,809,008 | 5/1974 | Takahashi | 118/425 |
| 3,903,908 | 9/1975 | Logue et al. | 118/425 |
| 3,976,028 | 8/1976 | Howells et al. | 118/6 |
| 3,986,518 | 10/1976 | Sato | 118/704 |
| 3,999,505 | 12/1976 | Kato et al. | 118/704 |
| 4,530,304 | 7/1985 | Gardos | 118/425 |
| 4,543,236 | 9/1985 | Von Gise | 118/702 |
| 4,738,824 | 4/1988 | Takeuchi | 422/63 |
| 4,911,098 | 3/1990 | Tabata | 118/423 |
| 4,966,094 | 10/1990 | Yamada | 118/698 |
| 5,023,187 | 6/1991 | Koebler et al. | 427/4 |

FOREIGN PATENT DOCUMENTS

| | | |
|---|---|---|
| 0323130 | 7/1989 | European Pat. Off. |
| 2196428 | 4/1988 | United Kingdom. |

Primary Examiner—Diana Dudash
Attorney, Agent, or Firm—Burns, Doane, Swecker & Mathis, L.L.P.

[57] ABSTRACT

A process and device are disclosed for dyeing histological specimens arranged on microscope slides. The microscope slides are transported by a conveyor (18) in object slide holders to processing stations (16) where they are subjected to processing steps that correspond to a selectable dyeing process. The conveyor (18) is designed in such a way that each object slide holder (14) is separated therefrom after entering a processing station (16), so that during the time a processing step is carried out in said processing station other object slide holders (14) can be transported to free processing stations (16) according to the selected dyeing process.

42 Claims, 7 Drawing Sheets

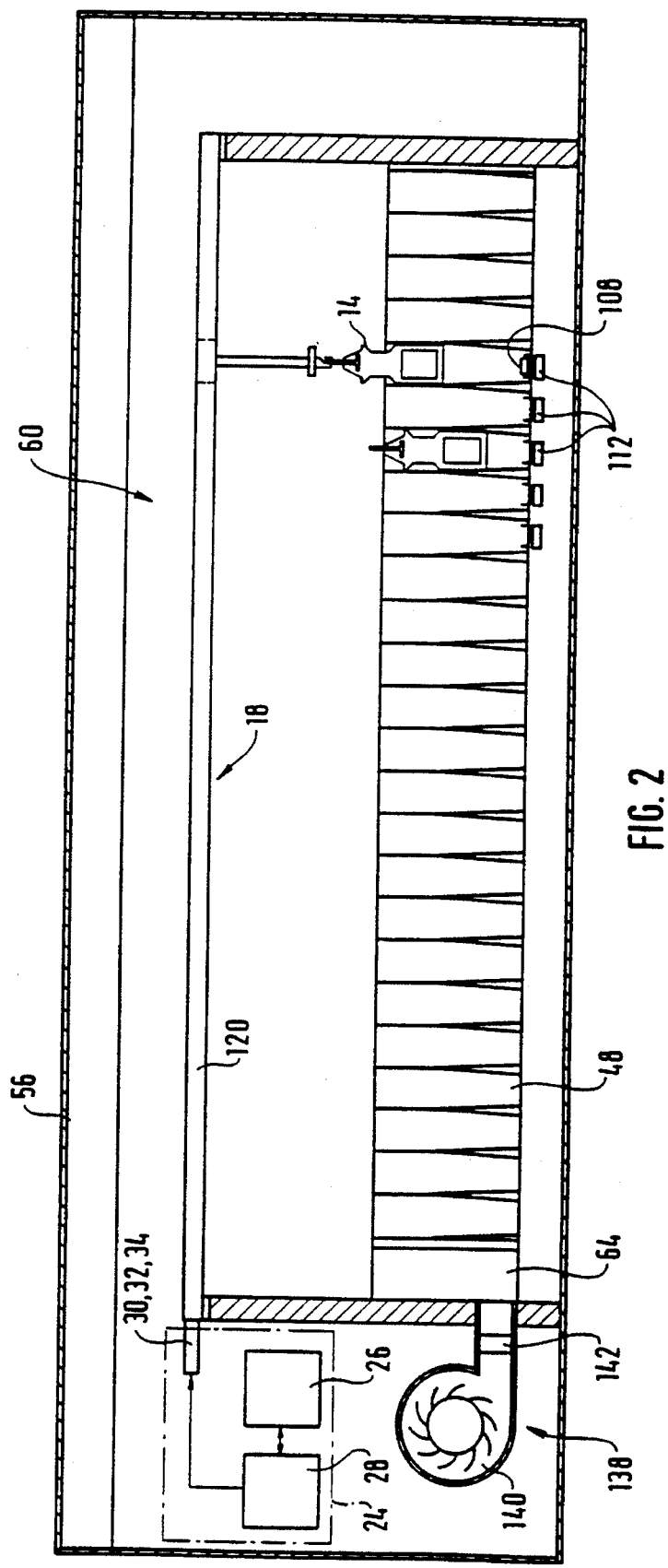

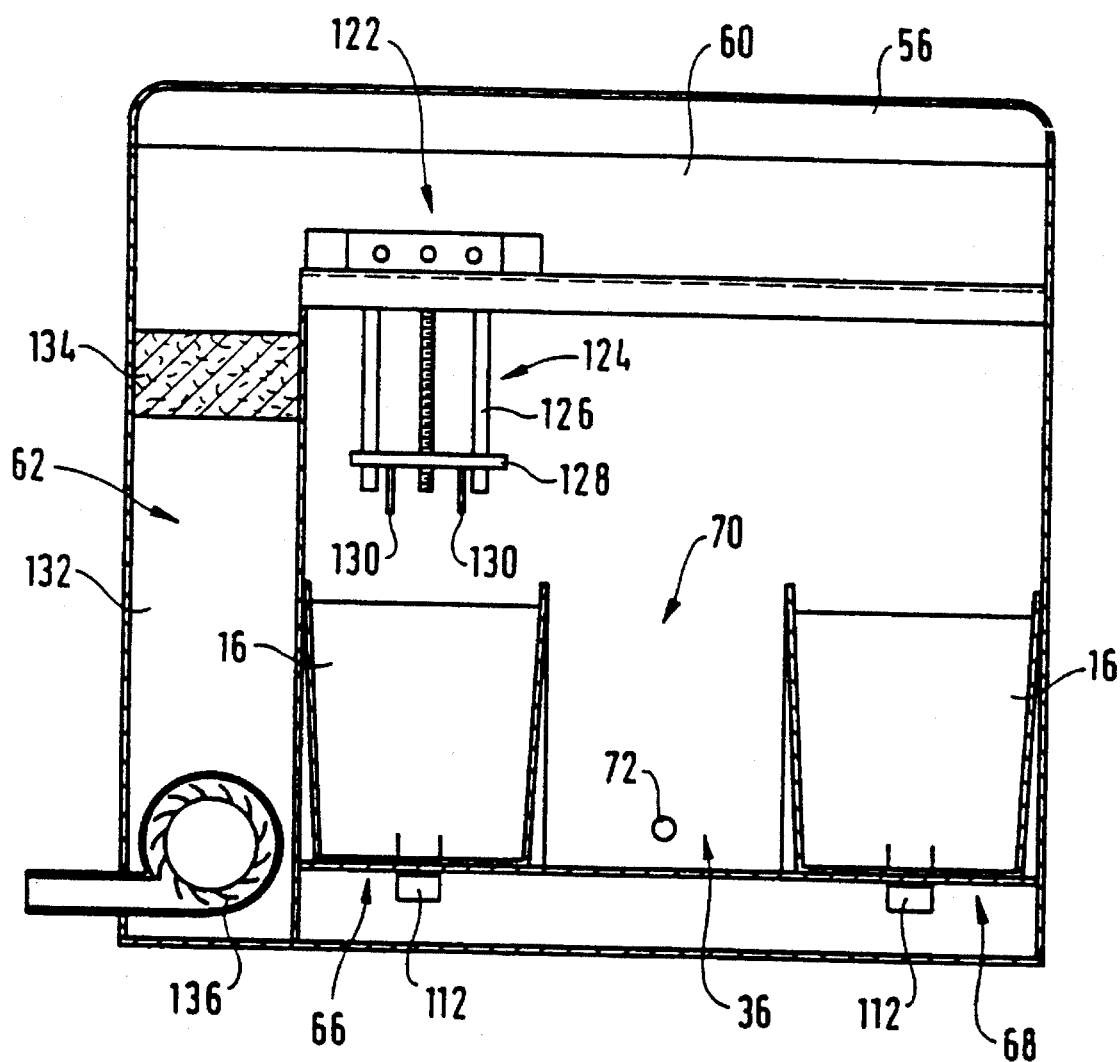

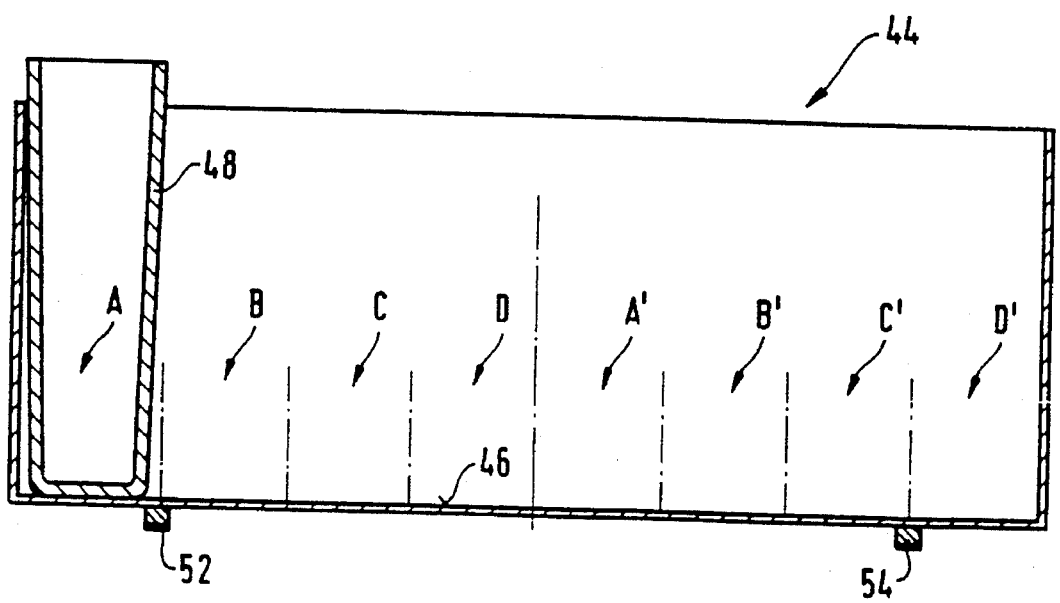
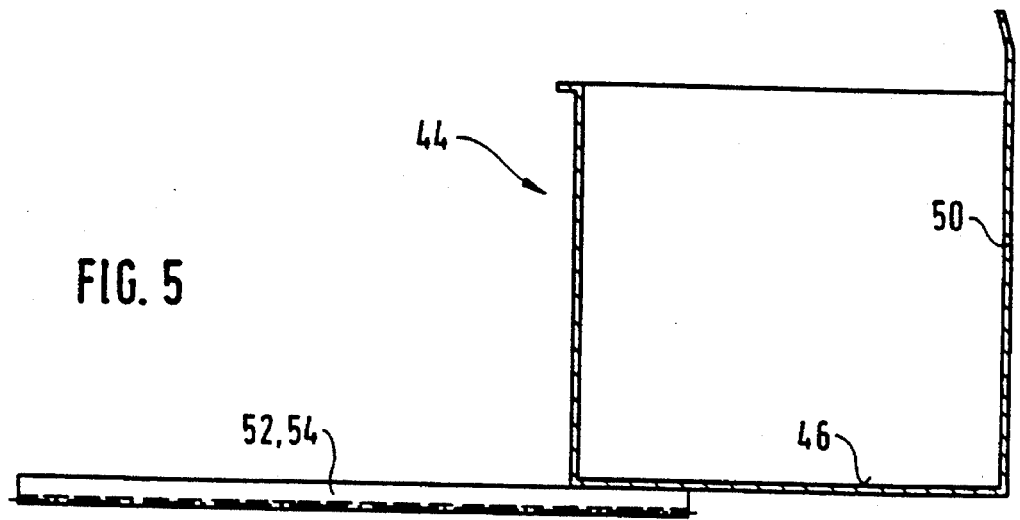

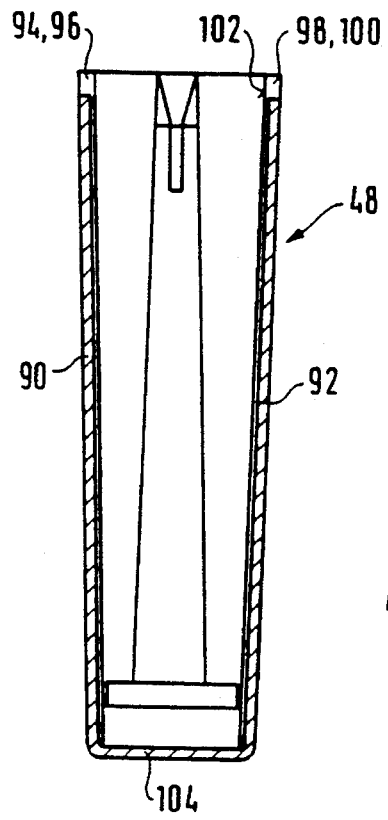
FIG. 7
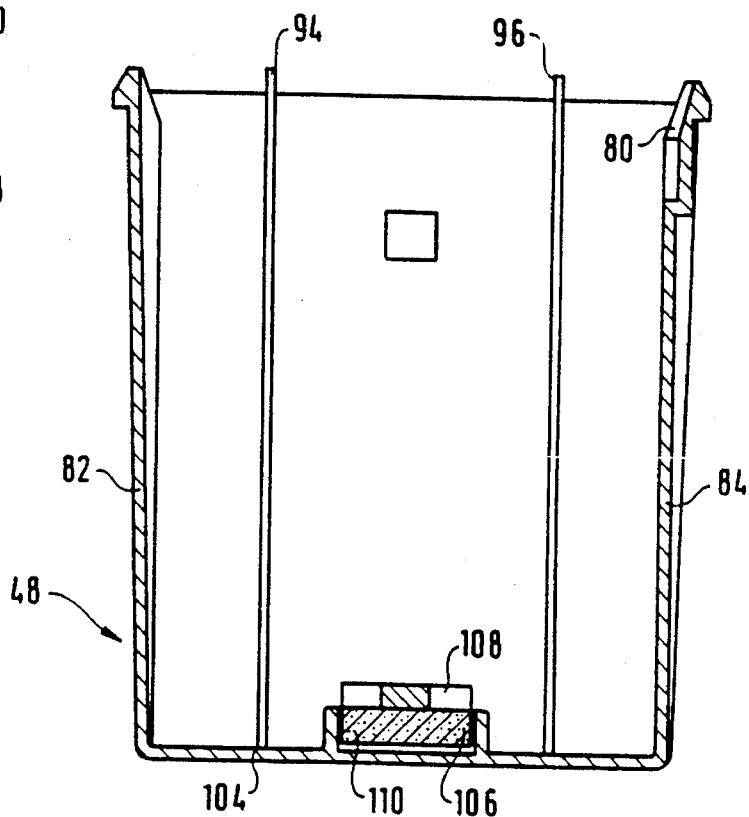
FIG. 6
FIG. 8
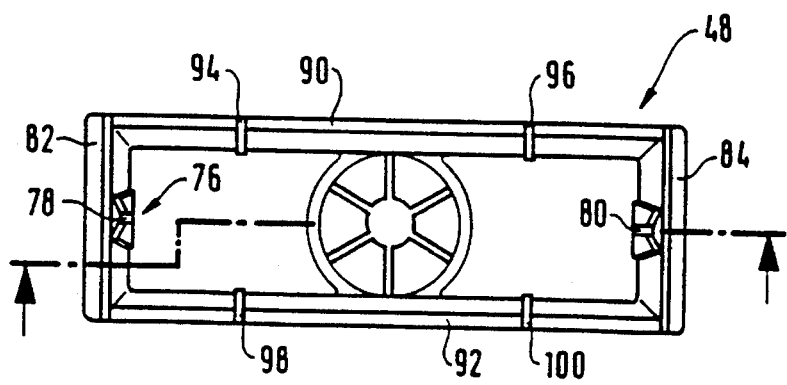

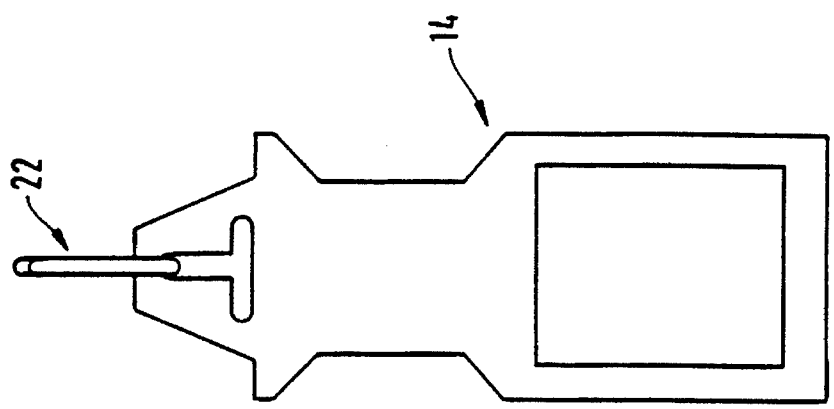
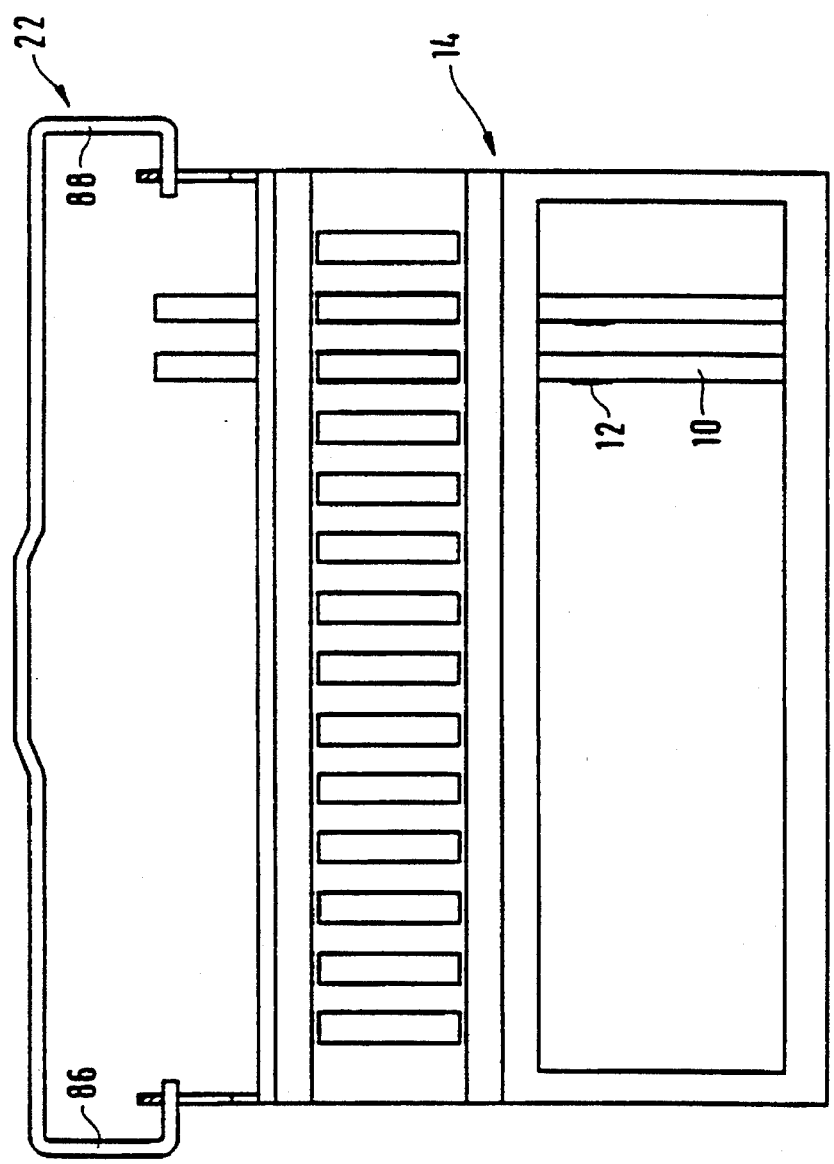

PROCESS AND DEVICE FOR DYEING HISTOLOGICAL PREPARATIONS ARRANGED ON MICROSCOPE SLIDES

BACKGROUND OF THE INVENTION

The invention relates to a process for dyeing histological preparations arranged on microscope slides.

When histological preparations are examined under a microscope, dyeing is one of the most frequently used methods to differentiate the structures in cells and tissues and to render them visible through high contrast. By suitably controlling the dyeing process individual structures can be selectively emphasized.

In dyeing histological preparations for microscopic examinations, the physical and chemical properties of the structure in the cells and tissues are utilized for binding specific dyes. For histological dyes, natural dyes are used, but predominantly synthetic dyes. Most of them are diachromes, i.e. they absorb in the range of visible light; others glow only with ultraviolet radiations; they are fluorescent dyes. What is important for the dyeing process is the charge of the dyes. There are electronegative, electropositive and neutral charges. When several dyes are used, they are either applied in succession or simultaneously in a dye solution.

To date, 80% of the histological preparations were dyed by dangerous manual labor and only 20% were dyed fully automatically. The reason lies in the fact that the automatic dyeing machines offered on the market can do only one dyeing method at a time currently and have to be refitted or reprogrammed when the dyeing method is changed.

A well-known automatic dyeing machine of the "Medite" company functions according to the principle of a continuously recurring transport movement for the object slide holders, in which microscope slides with histological preparations are situated. With this transport movement the object slide holders are transported to processing stations, of which there are up to 23 in succession. One object slide holder suspended into a first position of a sprocket is conveyed by the sprocket via a specific path as far as the processing station and lowered there into a first vat with a reagent. In so doing, during the processing time an additional reciprocating motion (agitation) can be conducted. Finally the object slide holder is lowered completely into the vat and the sprocket travels back again the same path under the carrying strap of the object slide holder. As soon the starting position is reached, a second object slide holder can move up into the first position of the sprocket.

Having carried out this process step, the sprocket lifts the first object slide holder out of the reagent, holds it according to a preselectable drip period above the vat and travels then one position further to the next processing station. There the first object slide holder is lowered into the second vat; and the second object slide holder, into the first vat. According to this principle the object slide holders travel through all of the processing stations and can finally be removed at the end of the carriage. The cycle time for the transport movement can be freely chosen within a specified frame and is the same for all processing stations. Different processing times can be obtained by connecting identical processing stations serially.

Another well-known automatic dyeing machine of the "Shandon" company functions according to the revolving method. In this case 24 processing stations, which can be freely selected, are arranged in a circle. However, the order of sequence in which the processing stations can be entered is fixed by the revolving method. Above the processing stations is a cover, which can be moved up and down and rotated clockwise. The object slide holders with the preparations, which are to be dyed and are arranged on microscope slides, are suspended from this cover and transported to the processing stations. During the dyeing process the cover can be agitated. Another function of the cover is to protect against the evaporation of the reagents. The protecting function is, however, operative only in the lowered state. The processing time in the individual stations can be programmed individually for each of the 24 processing stations. It is also possible to store two different dyeing programs, which can then be called by means of a push button when needed. However, these dyeing programs cannot run simultaneously.

An automatic dyeing machine of the "Sakura" company provides a matrix-shaped arrangement of the processing stations, which can be approached by way of a triaxial controller. There exists access to each processing station, so that a dyeing operation can be conducted in any arbitrary order, but only one dyeing method can be conducted at a time.

A device for automatic dyeing of preparations for microscopic examination is known from the GB-A-2 196 428. The prior art device includes several processing stations, to which histological preparations arranged on microscope slides are conveyed in object slide holders and are subjected there to processing measures corresponding to a selectable dyeing method. The conveyor includes coupling elements, which after placing an object slide holder into a processing station can be detached from it, so that a connection with another object slide holder is enabled. The conveyor is controlled in such a manner by a controller, into which the dyeing program must be fed prior to the implementation of each dyeing operation, that it can transport, as a function of the selected dyeing method, the other object slide holders to free processing stations.

Storage of different dyeing programs, which can be called, as desired, and run simultaneously in the sense of computer-controlled optimization, is not provided.

An automatic dyeing machine is known from the document U.S. Pat. No. 3,674,040; said automatic dyeing machine comprises two rows of baths with dyeing reagents, where the rows are arranged on two levels at a time. Object slide holders can be conveyed by means of a conveyor, which can be raised and lowered and moved only in the transverse direction to the insert positions of the baths. A specific approach of the baths is not possible. Rather the baths themselves have to be moved to the corresponding insert positions, whereby the baths on each level are coupled together like a chain and can be moved jointly and whereby the transfer from one level to the other is conducted with the aid of lifts at the beginning and end of the row. In so doing, the movement sequence of the chain and that of the lifts is limited only to one direction of movement.

Between the rows of baths there is a rinsing chamber, above which object slide holders in a central position of the conveyor can drip or be immersed and rinsed.

Furthermore, it is provided that the reagents can be circulated by means of agitator blades, which can be set rotating by means of a driver, moved in from the opening side of the baths.

SUMMARY OF THE INVENTION

The invention is based on the problem of improving a process for dyeing histological preparations arranged on microscope slides to the effect that the conditions are provided for processing preparations in parallel according to different dyeing methods.

The process according to the invention eliminates the limitations of the prior art automatic dyeing machines, with which only one dyeing method at a time can be conducted. In so doing, the processing time during which a microscope slide remains in a processing station is utilized to transport one or more other object slide holders to other processing stations. It is quite possible to subject the preparations in any object slide holder to another dyeing method. Yet, like the prior art automatic dyeing machines, it is also possible to transport several object slide holders in succession to the same processing stations in order to dye the preparations according to the same dyeing method.

Since the object slide holders are totally separated from the conveyor, the possibility of transporting other object slide holders to each processing station specified by the chosen dyeing method is provided. Thus, with the process according to the invention, it is also possible for such preparations that have to be dyed according to a dyeing method that is used relatively rarely and for which to date it did not seem worth the effort to refit the automatic dyeing machine to be dyed economically.

Moreover, the total time to dye different preparations is also dramatically reduced, since multiple dyeing processes can run in parallel and do not interfere with each other.

For each selectable dyeing method a program line is stored that includes the transport times, processing times, processing temperatures as needed and processing stations. The program start of different dyeing methods is automatically calculated in the sense of a non-overlapping parallel run of the program lines.

The result is an optimization of the time required, when several different dyeing methods are applied.

Furthermore, it is provided that the movement sequence of the conveyor between the individual processing stations is controlled in such a manner that an object slide holder to be transported is first gently accelerated out of the quiescent state, subsequently moved at constant velocity and finally gently decelerated.

This procedure achieves a very gentle transport and extensively avoids rocking movements of the object slide holders, from which dripping reagents could get into other processing stations and pollute them. Nevertheless, precisely in the case of long transport routes that are to be covered from one processing station to the next a short transport time is guaranteed. This in turn renders it possible to set the program start of different dyeing methods in such a manner that following the start of a dyeing process, the subsequent dyeing process can start at the earliest time possible.

Another embodiment provides that upon leaving a processing station with liquid reagents, the object slide holders are transported by way of a separate drip area to the next processing station.

With prior art automatic dyeing machines there were transport delays due to the fact that upon lifting a microscope slide out of a processing station with liquid reagents, one had to wait first until the still clinging reagents had dripped off. Not until then could the next processing station be approached, if polluting of other processing stations was not to be accepted. In the case, however, of the described embodiment, a transport route is taken that does not lead by way of other processing stations, but rather by way of a drip area. Thus, the time required in any event to drip off can be exploited for the transport.

In a practical embodiment the histological preparations that are to be dyed and are arranged on microscope slides are placed separately according to the dyeing methods to be conducted in object slide holders into a feed station. In a control program the position in the feed station is linked with a selected dyeing method. Then the object slide holders are transported in succession from the feed station to the processing stations, as soon as a parallel processing sequence is guaranteed; and following completion of the processing measures the object slide holders are placed into a removal station.

This measure has the advantage that several object slide holders with the preparations to be dyed can be put simultaneously into the feed station. Thus, one does not have to wait until an object slide holder was included in the process run, before the next object slide holder can be entered. Similarly, to remove the processed preparations, the object slide holder concerned does not have to be removed after each completed processing operation. Rather, one can wait until all of the object slide holders have gone through the processing process; and then all of them can be removed together and introduced to other examinations. In addition, the time is thus reduced in which, upon opening the device, harmful reagent vapors can escape. In addition, there is the possibility of also removing one or more object slide holders, as needed.

Furthermore, it is provided that the object slide holders in the removal station are placed in the same position in which they are also put into the feed station.

Thus, an unequivocal allocation of processed object slide holders is achieved. Thus, it is not necessary to mark them according to the selected dyeing method. Rather it Suffices to store the position in which they were put into the feed station. The risk of a possible confusion is thus avoided.

Another embodiment provides that the object slide holders are placed from the side into the feed station and removed from the removal station.

With this measure it is achieved that the most readily volatile reagents of the processing stations cannot escape or only to a small degree to the environment, when preparations that are to be processed and are arranged on their object slide holders are placed into the device or are removed as processed.

The preparations are processed, fed, and removed with the top side of the device closed to the environment. In addition, the reagent vapors are drawn off.

In this manner the concentration of reagent vapors in the interior of the device is reduced so that rising reagent vapors accummulate preferably in a space below the top-sided closure, instead of escaping by way of the deeper region of the feed and removal stations.

A practical embodiment also provides that in processing stations with liquid reagents the reagents are circulated during the processing period.

This measure replaces having the reagents wash around the preparations, said flowing around being achieved by the up and down movement of the object slide holders in the prior art automatic dyeing machines. Thus, an effective flowing around is achieved here, even though the object slide holders themselves remain stationary during the processing period in the processing station. In addition, during the circulation, the reagents are thoroughly mixed, thus avoiding changes in the concentration in the immediate vicinity of the surface of the preparations.

Furthermore, the processing can also take place in heated processing stations.

In this manner the processing time can be in part drastically reduced.

Furthermore, it is provided that before and/or after individual processing measures in the reagents a thermal processing measure is conducted.

Such processing measures can serve to dry the preparations on the microscope slides; or in the case of prepared preparations they can melt off a layer of wax that was originally applied by means of thermal impact and the preparation can be simultaneously attached to the microscope slide.

Furthermore, the invention relates to a device for dyeing histological preparations arranged on microscope slides.

In this respect the invention is based on the problem of providing a device that renders it possible to carry out different dyeing methods in parallel.

The problem is solved by a device according to the invention.

The device according to the invention is not restricted to conducting only one dyeing method at a time. Rather, in the time in which one object slide holder is deposited in a processing station and is processed there, one or more other object slide holders are conveyed to free processing stations and the preparations are subjected there to corresponding processing measures. During an on-going dyeing process, even several object slide holders with different preparations can be processed according to dyeing methods that are individually different. Thus, an automatic dyeing process is also economical for such dyeing methods that have to be rarely applied as compared to other dyeing methods and for which to date it was necessary to refit the automatic dyeing machine.

The controller existing in this device comprises a memory, in which for each selectable dyeing method a program line is stored that includes the transport times, processing times, processing temperatures as needed and processing stations. In addition, a computer is provided that controls the program start of different dyeing methods in order to obtain programs that run in parallel without overlapping.

Thus, several dyeing processes of also different dyeing methods can also run interlaced, without mutually interfering. The total time for several different dyeing processes to run can be reduced in this manner, since while one dyeing process is running, the next dyeing process can be started, as soon as it can be guaranteed that both dyeing processes can run without interference. This can be the case, when a first object slide holder has reached its first processing station and the conveyor is now in the position to pick up the next object slide holder and to transport it to the first processing station specified by the assigned dyeing method.

An advantageous embodiment provides that the controller comprises an actuator, which controls the movement sequence of the conveyor between the individual processing stations in such a manner that an object slide holder to be transported is gently accelerated first out of the quiescent state, subsequently moved at constant velocity, and finally gently decelerated.

This movement sequence allows a very gentle, but still speedy transport from one processing station to the next. The gentle acceleration and deceleration virtually prevent swivelling movements of the object slide holder, which could otherwise result in the still clinging reagents while dripping being thrown into the neighboring processing stations and polluting them. Yet the transport itself between remote processing stations is so fast that the program start of the next dyeing process is not delayed so as to be a disturbing factor.

In a practical embodiment of the device there is a separate drip area, above which the object slide holders are transported upon leaving a processing station with liquid reagents to the next processing station.

Due to the transport over the drip area waiting periods are avoided that were necessary with the prior art automatic dyeing machines, in order to enable the still clinging reagents to drip off after pulling the object slide holders out of a processing station with liquid reagents. The time spent during this operation can now be used economically for the transport, thus avoiding the need to cross over other processing stations on the transport route. The drops of reagent that are still adhering even after some drip time can no longer pollute other processing stations.

In a preferred embodiment the device exhibits a feed station for the arrangement of histological preparations that are to be dyed and are arranged on microscope slides; said arrangement being separated according to the dyeing method to be conducted. Furthermore, there is a removal station, in which object slide holders are deposited after conducting the processing measures. In a control program the position in the feed station is linked to a selected dyeing method; and the sequential transport of the object slide holders from the feed station to the processing stations is controlled in such a manner that parallel processing is guaranteed.

By means of the feed and removal stations it is possible to place several object slide holders at once into the device, in order to carry out the dyeing process. Thus, one no longer has to wait until the first object slide holder was picked up by the conveyor, before the next object slide holder can be inserted. Rather, the object slide holders are automatically removed and later deposited.

Furthermore, there exists the possibility of selecting from several stand-by object slide holders those object slide holders as the next ones whose program line can be tied the best into the program line of the dyeing method that is currently running. Thus, when several different dyeing methods are running, the total time of all of the dyeing methods can be minimized.

Furthermore, the feed station and the removal station exhibit positions for inserting and depositing the object slide holders; and the conveyor is controlled in such a manner that the object slide holders in the removal station are placed into the same position in which they were also put into the feed station.

The result is that the preparations are uniformly assigned to the completed dyeing method, so that only the position of the object slide holders have to be stored; special marking or labelling of the object slide holders can be dispensed with. Thus, handling is easier without the risk of confusion.

Preferably the feed station and the removal station have a front-sided access in a housing enclosing the device.

This kind of access prevents excessive amounts of reagent vapors from escaping. The reagent vapors usually rise to the top, owing to their lower specific weight compared to air, so that in the upper region of the housing a higher concentration remains than in the bottom region. Thus, reagent vapors of higher concentration remain in the device itself.

Another embodiment provides that the feed station and the removal station include a horizontally moveable drawer and that in the pushed-in position of the drawer the conveyor has access to the object slide holders, whereas in the pulled-out position the object slide holders are inserted or removed by hand.

This design of the drawer enables the object slide holders to be put conveniently into the drawer from the top, and then all of the inserted object slide holders to be pushed with one movement into the device, or already processed preparations in the object slide holders to be pulled out of the device. By inserting from the top it is possible to position the object slide holder in a simpler manner. In addition, the opening time of the device that is required to refeed and remove can be thus reduced, a feature that, on the one hand, has a positive effect on the efficiency of the dyeing process and, on the other hand, reduces to a minimum the escaping of the vapors of the reagents.

In an advantageous embodiment of the drawer, a parallel guide is provided. It comprises two toothed racks, which engage with gear wheels, disposed on a common shaft.

When the drawer has a low installation depth, this parallel guide guarantees a faultless pulling out and pushing in, since no tilting can occur.

In a practical embodiment the drawer exhibits a bearing surface for vats, in which the object slide holders in the feed station and the removal station are stored. In addition, it exhibits a vertical outer wall, which in the pushed-in state closes an opening in the housing of the device. In addition, a seal can be arranged between the vertical outer wall of the drawer and the wall region with the opening in the housing.

In the pushed-in state of the drawer the vertical outer wall causes the entire housing to be totally closed and thus no reagent vapors can escape to the outside in an uncontrolled manner. In so doing, the drawer can be designed in such a manner that it is flush with the outer wall and no protruding parts protrude into the space, so that workers cannot catch their clothing inadvertently on said parts.

Another embodiment provides that between the opening in the housing and at the upper cover there is a vertical and/or oblique wall region, which together with the remaining wall region and the upper cover also forms in the pulled-out state of the drawer a collecting space for the reagent vapors.

Since reagent vapors with a lower specific weight than air rise to the top, they collect preferably in the collecting space, instead of flowing through the lower lying opening in the housing when the drawer is pulled out. The result is that the operators are exposed to significantly less pollution with reagent vapors, as was still the case with prior art automatic dyeing machines and in particular with the manual dyeing method.

Preferably the collecting space is connected to an exhauster. This exhauster provides that the concentration of reagent vapors in the collecting space is below the saturation limit and prevents in this manner also higher concentrations in the bottom regions. This has a positive impact, when the drawer for inserting new preparations to be processed or for removing dyed preparations has to be opened, since the concentration of the escaping reagents is dramatically reduced.

The device according to the invention comprises processing stations, in which vats with reagents stand, and a drying chamber.

Cleaning and rinsing fluids or also dyes can be disposed in the vats. The exact arrangement is in principle of a subordinate importance, since to carry out a specific dyeing method not the kind of arrangement but only the knowledge of the arrangement is important for the control program. Thus, it is usually unnecessary to provide several processing stations with the same reagent, since the residence times of the object slide holders in the processing stations can be controlled individually. Insofar as the reagents for different dyeing methods exist totally in individual processing stations, all of the dyeing methods can also be programmed and implemented by choice.

A preferred configuration of the processing stations in the device provides that they are arranged in two parallel rows in the housing. The separate drip area is arranged between two parallel rows with processing stations.

Thus, a compact construction is obtained and the transport routes for the worst transport case of processing stations that are diagonally across from each other can be decreased in this manner.

In this configuration one can make do with a single drip device, since it is available both for processing measures in the processing stations on the one row and also on the other row. Especially when one has to change from one row to the other row when changing the processing stations to be approached, the approach of the drip station does not represent a detour on the transport route.

Expediently the separate drip area is designed as a chamber, through which water flows and which exhibits an inlet and an outlet.

Thus, it is possible, on the one hand, to rinse preparations on object slide holders also in this chamber through which water passes; on the other hand, the dripping reagents can be removed by a simple method from the device.

In particular, when the chamber through which water passes is also supposed to be used simultaneously for cleaning purposes, a high degree of purity can be reached by continuously changing the water.

To pick up the object slide holders in the processing stations, holding elements can be provided. In a preferred embodiment they are designed as open blind slots in two opposite inner walls of the vats or the drying chamber. During insertion, laterally protruding legs of the coupling elements of the object slide holders slide into these blind slots.

The blind slots serve to define both sideways and depth position. These two kinds of fixed positioning make it easier for the conveyor to recouple a deposited object slide holder and to lead it to the next processing station.

Furthermore, the inner walls of the vats and drying chambers exhibit spacing and/or guide rods.

These spacing and/or guide rods also provide for a defined position of the object slide holders in the respective processing station. In addition, they ensure a gap between the preparations and the inner wall, so that unimpeded wetting of the preparations with the reagents or in the drying chamber with the drying air is enabled.

Expediently the spacing and/or guide rods are arranged in pairs on the two inner walls.

Thus, it is prevented that the object slide holders can tilt within the vats or the drying chamber. The guiding by pairs by means of the spacing and/or guide rods improves the precision of the position occupied upon inserting the object slide holders.

Another embodiment provides that the spacing and/or guide rods protrude beyond the upper rim and exhibit inlet slopes.

These inlet slopes provide that the object slide holders slide faultlessly into the vat or the drying chamber even when the conveyor misses slightly the position when approaching the processing stations, or the vats in the processing stations are laterally offset. In addition, the object slide holders can be lowered, even when following the gentle deceleration of the conveyor a slight oscillation of the object slide holders has not subsided yet.

Another embodiment provides that the vats are made of non-magnetic material; and cup-shaped compartments for agitator blades are arranged in the floors of the vats.

With the aid of these agitator blades, circulation of the reagents in the vats is possible, even when the object slide holders rest immoveably in the mountings and cannot be moved to and for by the conveyor. Due to the design of the vats made of non-magnetic material, the conditions for a magnetic drive of the agitator blades are provided.

In this respect another embodiment provides that armatures made of a soft magnetic material or permanent magnets are integrated into the agitator blades.

In this manner the agitator blades simultaneously form a part of a magnetic coupling or the rotors of the drives which can be mounted outside the vats. The advantage of a magnetic coupling is that no rotatable parts have to be run through the walls of the vats. Thus, sealing elements can be dispensed with that increase in an undesired manner the torque to be produced and with time begin to leak due to wear.

Preferably agitator drives that are magnetically coupled to the armatures or permanent magnets of the agitator blades are arranged below the vats in the processing stations.

With this arrangement the goal is reached that the drives can remain stationary in the housing bottom, when individual vats have to be removed or replaced with others. In this manner the filling or replacement of consumed reagents is simplified.

Another embodiment provides that one or more processing stations can be heated.

By means of heating, different temperatures for different reagents can be set so that in some processing stations the residence time of the preparations can be shortened owing to the higher processing speed. This feature, too, contributes to reducing the total time required when using single or several different dyeing methods.

In a practical embodiment the heatable processing stations are arranged side-by-side.

Thus, undesired energy losses incurred through radiation can be reduced; and, above all, heat transmission to processing stations, which are not to be heated, can be avoided. The possibility of setting up an area, in which heatable processing stations are concentrated, is given by the fact that the processing stations can be approached by choice by means of the conveyor; and, therefore, the order of sequence in which processing measures with or without heated reagents are to take place is not a factor. Thus, the area, in which heatable processing stations are arranged, can also be chosen from the point of view of the smallest possible electric stray radiation on electronic components of the controller.

The heating elements can be alternated in the housing below the vats and be coupled thermally to the vats or also attached to the vats themselves.

The first alternative has the advantage that the construction of the vats in the heatable processing stations can be identical to that in unheatable processing stations; and, therefore, the vats can be readily replaced.

The second alternative requires special vats, but facilitates the thermal coupling between the heating elements and the vats.

In another embodiment of the second alternative heating elements are arranged on the underside of the floors and the outsides of the walls.

The result is an especially narrow thermal coupling between the heating elements and the vats, thus achieving that the thermal energy is effectively transferred to the reagents, instead of being emitted to the environment. The arrangement both at the floors and also the outer walls of the walls guarantees a uniform distribution and thus a homogeneous heating of the reagents. Due to the large areal thermal transmission the need to have to raise the heating elements to a very high excess temperature over the targeted heating temperature of the reagents can be dropped.

The heating elements can also be integrated into the floors and/or into the walls.

The result is an even better coupling of the thermal energy into the reagents.

In a practical embodiment the temperature probes and the regulating circuits, connected to the temperature probes and the heating elements, are provided. The temperature probes are thermally coupled to the floors or the walls of the vats.

Thus individual temperatures can be set for each processing station; and the heat losses occurring due to evaporation, radiation or thermal transfer to the microscope slides are individually and quickly compensated for, so that the temperature that is necessary for optimal processing is always guaranteed.

Preferably regions on the underside of the vats below the compartments are recessed from the heating elements and the temperature probes.

Thus, even for heatable vats a faultless magnetic coupling is produced between the drives and the agitator blades.

The lifting and lowering device of the conveyor exhibits a parallel guide, which comprises two guide rods, for the coupling element.

Thus, the goal is achieved that the coupling element remains horizontally aligned, even when the object slide holder to be transported is equipped or loaded on one side.

Other designs and advantageous embodiments of the invention follow from the claims, the additional description and the drawings that illustrate an embodiment.

BRIEF DESCRIPTION OF THE DRAWINGS

FIG. 2 is a longitudinal view of the device according to FIG. 1.

FIG. 3 is a cross sectional view of the device according to FIG. 1.

FIG. 4 is a longitudinal view of a drawer.

FIG. 5 is a cross sectional view of a drawer.

FIG. 6 is a longitudinal view of a vat.

FIG. 7 is a cross sectional view of a vat.

FIG. 8 is a top view of a vat.

FIG. 9 is a longitudinal view of an object slide holder.

FIG. 10 is a cross sectional view of an object slide holder.

DETAILED DESCRIPTION OF THE INVENTION

Figure 1:
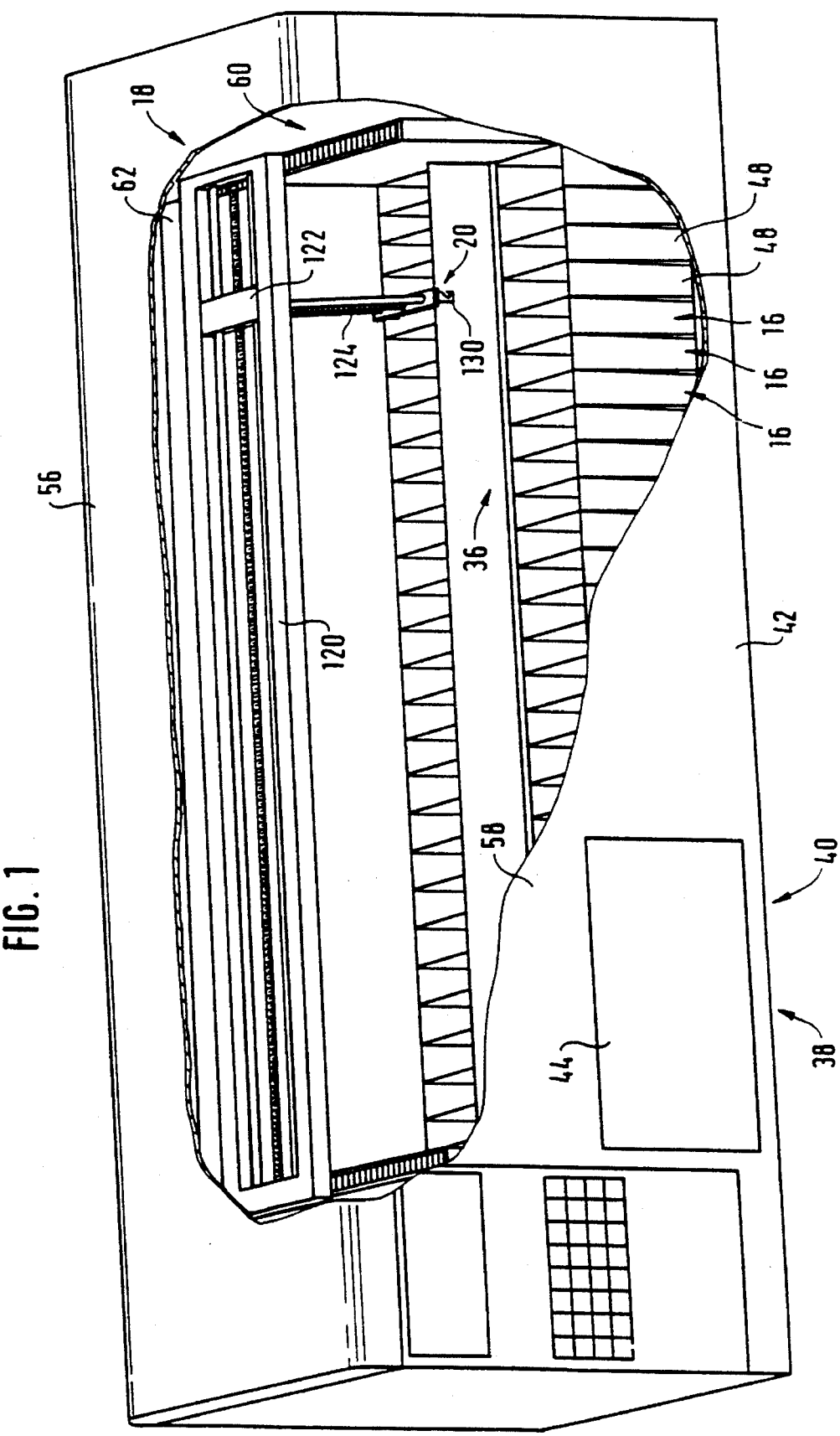
FIG. 1 is a perspective view of a device according to the invention that is partially broken away.

The FIGS. 1 to 3 show a device for dyeing histological preparations arranged on microscope slides.

The device comprises a housing 42 with several processing stations 16. The processing stations 16 have vats 48 with reagents for preprocessing and dyeing and a drying chamber 64.

The processing stations 16 form in the housing 42 two parallel rows 66 and 68; and between these rows there is a drip area 36, which is designed as a chamber 70 through which water passes. A conveyor 18 is arranged above the processing stations 16. Furthermore, a feed station 38 and a removal station 40, which includes a horizontally moveable drawer 44, are provided in the front region of the housing 42.

The conveyor 18 enables transport movements in three coordinate axes. Thus, the processing stations 16 can be approached in any arbitrary order. A first transport carriage 120 can be moved in the cross direction. It rests on two housing-sided rails and is equipped with a parallel drive, which ensures a synchronous movement on both tracks.

A second transport carriage 122 for a movement in the longitudinal direction is arranged on the first transport carriage 120. Since the span width of this second transport carriage 122 is smaller, it can make do without a parallel drive. The second transport carriage 122 in turn carries a lifting and lowering device 124. The two transport carriages 120 and 122 and the lifting and lowering device 124 are driven by actuators 30, 32, and 34, which are designed as stepping motors, or regulated direct current motors as servomotors. The position reached is detected by means of sensors, which are not shown here for reasons owing to a better overview. This design enables a very exact, repeatable positioning.

The actuators 30, 32, and 34 are a component of a controller 24, which also includes a computer 28 and a memory 26.

As especially apparent from FIG. 3, the lifting and lowering device 124 exhibits a parallel guide for a coupling element 20. The coupling element 20 comprises a carrier plate 128 and two parallel gripper hooks 130, which are spaced apart.

These gripper hooks 130 are adapted to the corresponding coupling elements 22 on the sides of the object slide holders 14. The latter are shown in FIGS. 9 and 10. As apparent from the drawing, the coupling elements 22 are formed by the handles of these object slide holders 14.

The gripper hooks 130 are coupled to the coupling elements 22 of the object slide holders 14 in that the object slide holder 14 to be picked up is first approached from a longitudinal side, where the gripper hooks 130 are lowered so far that they are deeper than the coupling elements 22 of the object slide holders 14. If the gripper hooks 130 and the coupling elements 22 are aligned, the lifting and lower device 124 is lifted and the coupling takes place in that the handle of the object slide holder 14 concerned rests in the depression of the gripper hooks 130 and is raised.

The object slide holder 14 can be moved now only to the predetermined position by moving the two transport carriages 120 and 122 in a corresponding manner. Upon reaching the desired position the lifting and lowering device 124 is lowered until the object slide holder 14 rests on a mounting of the processing station 16.

Then the gripper hooks 130 move a little further downwardly until the handle has detached itself from the gripper hooks. Thereafter the second carriage 122 is moved again; and subsequently another object slide holder 14 can be picked up in a similar manner.

The conveyor 18 is operated with the controller 24. A program line, which consists of transport times, processing times, processing temperatures and processing stations 16 to be approached, is stored in the memory 26. Depending on the selected dyeing method a specific program line, which causes the computer 28 to control the movement sequence by way of the actuators 30, 32, and 34, is selected in the memory 26. When several different dyeing methods run simultaneously, the program start of different dyeing methods is controlled with the aid of the stored program lines in the sense of a non-overlapping parallel run of the program lines. Thus, if, for example, the dyeing process is initiated for a first object slide holder 14, then the program determines with the aid of the program line of the dyeing method for the on-going dyeing method and the program lines for other dyeing methods the start time at which the next dyeing method can begin. As soon as this start time is reached, the next object slide holder 14 is included in the processing sequence.

To prepare a dyeing method, preparations 12 on microscope slides 10 are inserted into object slide holders 14, as shown in FIG. 10; and the object slide holders 14 are placed in a feed station 38. The object slide holders 14 are automatically taken in succession by the conveyor 18 from this feed station 38 and conveyed to the processing stations 16 provided by the program with the aid of the selected dyeing methods. Upon completing the dyeing process the object slide holders 14 are placed into a removal station 40.

The feed station 38 and the removal station 40 are accessible by a side opening in the housing 42. The insertion of prepared object slide holders 14 or the removal of processed object slide holders 14 takes place by way of a horizontally moveable drawer 44, which is shown in detail in the FIGS. 4 and 5.

The drawer 44 exhibits a bearing surface 46, on which vats 48 for the object slide holders 14 can be deposited. Positions A, B, C and D, to which object slide holders 14 in the feed station 38 go, are marked on the left side; whereas corresponding positions A', B', C' and D', in which the processed object slide holders 14 in the removal station 40 are placed, are marked on the right side. Thus, the program provides that after carrying out the dyeing process the object slide holders are placed in the same position in the removal station 40 in which they were also put in the feed station 38.

In the pushed-in position of the drawer 44 the conveyor 18 has access to the object slide holders 14, whereas in the pulled-out position of the drawer 44, it is possible to manually insert and remove the object slide holders 14. Two toothed racks 52 and 54, which engage with gear wheels arranged on a common shaft, provide for a parallel guide of the drawer 44 both for automatic and manual operations.

The drawer 44 exhibits an upright, in this case perpendicular, outer wall 50, which in the pushed-in state closes an opening in the housing 42 of the device. A seal can also be arranged between the outer wall 50 of the drawer 44 and the wall region with the opening in the housing 42.

As the detailed drawing of the drawer 44 in connection with FIG. 1 shows, there is a vertical wall region 58 between the opening in the housing 42 and an upper cover 56. It defines together with the remaining wall region and the upper cover 56, also in the pushed-out state of the drawer 44, a collecting space 60 for reagent vapors.

Whereas in the closed state of the drawer the opening is sealed in any event and thus no reagent vapors can escape to the outside, an uncontrolled escape of reagent vapors is also prevented in the opened state when inserting or removing the object slide holders 14. Owing to its lower specific weight as compared to air, the reagent vapors rise to the top and concentrate in the collecting space 60, so that in the bottom region of the housing 42 only vapors of smaller concentration dwell and thus an escape through the opening is dramatically reduced. The concentration of the reagent vapors in the collecting space 60 is also decreased by means of an exhauster 62, which is connected to the collecting space 60 and is arranged in the rear portion of the housing 42, thus further reducing a noticeable escape of reagent vapors when the drawer 44 is opened. The exhauster 62, shown in FIG. 3, comprises an air channel 132 with a charcoal filter 134 at the inlet and one or more ventilators 136. After being thoroughly cleaned by the charcoal filter 134, drawn off vapors are led out by way of a pipe attached to the rear side.

The processing stations 16 in the housing 42 of the device are situated at precisely defined places, which are also stored in the control program of the controller. Thus, said processing stations can be specifically approached. The vats 48, which stand in the processing stations 16, contain as reagents cleaning and rinsing agents and the actual dyeing reagents. A specific order of reagents in the processing stations 16, which is related to the program run, is not necessary, since all of the processing stations 16 can be approached in a short period of time and there is constant access to any processing station 16. Yet it can be logical to set up the processing stations 16 with reagents for the most frequent dyeing methods in such a manner that short transport routes between the individual stations can be achieved.

These short transport routes can be achieved, among others, by arranging the processing stations 16 in two parallel rows 66 and 68 with a drip area 36 between the processing stations 16. This drip area 36 is preferably designed as a chamber 70, through which water flows, and has an inlet 72 and an outlet, so that the water polluted by the dripping reagents can be changed. In addition to the function as a drip area, this chamber 70, through which water flows, can also be used as another processing station in which the object slide holders 16 with the microscope slides are watered.

One special advantage of the chosen arrangement lies in the fact that during transport from one processing station 16 to the next, the path can always be taken by way of the drip area 36, so that, on the one hand, the reagents are prevented from being dragged to the next processing station 16 and the risk of polluting the same is prevented. On the other hand, the transport route is also used for the still adhering reagents to drip from the microscope slides. Waiting periods, which are necessary in the case of prior art automatic dyeing machines, in order to avoid polluting the processing stations with foreign reagents, are, therefore, nonessential.

The drying station 64 represents a special processing station without reagents. It is located on the rear left wall and is connected to a warm air blower 138, which is arranged in the left region of the housing 42 and is evident from FIG. 2. The warm air blower comprises the actual blower 140 and a heater 142 in the air channel. The temperature of the warm air can be detected by a temperature probe and controlled by a regulating circuit, which can also be formed by the computer 28.

In contrast to prior art dyeing vats, as used in conventional automatic dyeing machines, the vats 48 used here are characterized by special constructive features. As apparent from FIGS. 6, 7 and 8, the vats 48 include holding elements 76 for inserted object slide holders 14. These holding elements 76 consist of blind slots 78, 80, which are open at the top, in two opposite inner regions of the walls 82 and 84.

Sideways protruding legs 86, 88 of the object slide holders 14 slide during insertion into these blind slots 78, 80. In the pushed-in state the legs 86, 88 of the object slide holders 14 rest on the bottom end of the blind slots 78, 80.

The projecting legs 86, 88 are connected at the top by means of a connecting leg and form a handle. These handles, which serve simultaneously as coupling elements 22, are tentatively fixed in an upright position, so that they can be grasped by the conveyor 18, in particular their gripper hooks 130.

As also apparent from the drawing, the other inner regions of the walls 90 and 92 have spacing and/or guide rods 94, 96, 98, 100. The spacing and/or guide rods 94, 96, 98, 100 are arranged in pairs on the two inner walls 90, 92. They provide that the object slide holders 14 are positioned exactly in the vats 48 or the drying chamber 64. Thus, the depositing and picking up by the conveyor is facilitated; on the other hand, a space remains between the object slide holders 14 and the walls of the vats 48, so that the reagents can also circulated, as needed, and thus flow unimpeded to the preparations 12 on the microscope slides 10.

To facilitate the insertion of the object slide holders 16 into the vats 48, the spacing and/or guide rods 94, 96, 98, 100 exhibit inlet slopes 102, which project beyond the upper rim. If slight shifts occur during insertion, the inlet slopes 102 provide that these positioning errorsare compensated. Thus, the legs 86 and 88 of the object slide holders 14 slide exactly into the blind slots 78 and 80.

Yet even if there are no positioning errors, the inlet slopes 102 help accelerate the process sequence, since one does not have to wait until the pendulum movements of the object slide holders 14 have subsided when the conveyor 18 is stopped. Rather the object slide holders 14 can be lowered immediately upon reaching the processing position. Then, upon entering, the pendulum movements are intercepted by means of the inlet slopes 102 of the spacing and/or guide rods 94, 96, 98, 100.

As evident from the detailed drawings of the vats 48, the vats 48 exhibit cup-shaped compartments 106 in the floors 104. Agitator blades 108 can be arranged in these compartments 106. These agitator blades 108 render it possible to circulate, as necessary, the reagents, so that reagents can effectively wash around the preparations even when the object slide holders 14 are resting.

The vats 48 are made of non-magnetic material; and agitator drives 112 are arranged underneath the vats 48. The agitator blades 108 include integrated permanent magnets 110 and are coupled magnetically to the agitator drives 112. The agitator drives 112 can also be equipped with a magnetic coupling as the mechanical drive or as synchro generator. The latter design is preferred, since then one can dispense with moveable elements, which are attached stationarily in the housing.

The agitator drives 112 can remain constantly in their place, so that the vats 48 can be removed without further ado, when the reagents have been consumed or are replaced, and said vats can be reinstalled or replaced. In so doing, no measures to uncouple the drive 112 from the agitator blades 108 are necessary.

Specific dyeing methods also require thermostated reagents. To this end, some processing stations are designed to be heatable. The heatable processing stations 16 are arranged preferably side-by-side, so that thermal losses are not transferred to unheated processing stations and the entire consumption of energy is reduced by concentrating the heatable processing stations.

Even the possible source of electric interference signals owing to the regulating operations of the integrated regulating circuits can be concentrated in one region, whereby by means of a suitable arrangement of this region the disturbing influence of other components, e.g. the controller for the conveyor can be decreased or eliminated.

Figure 11:
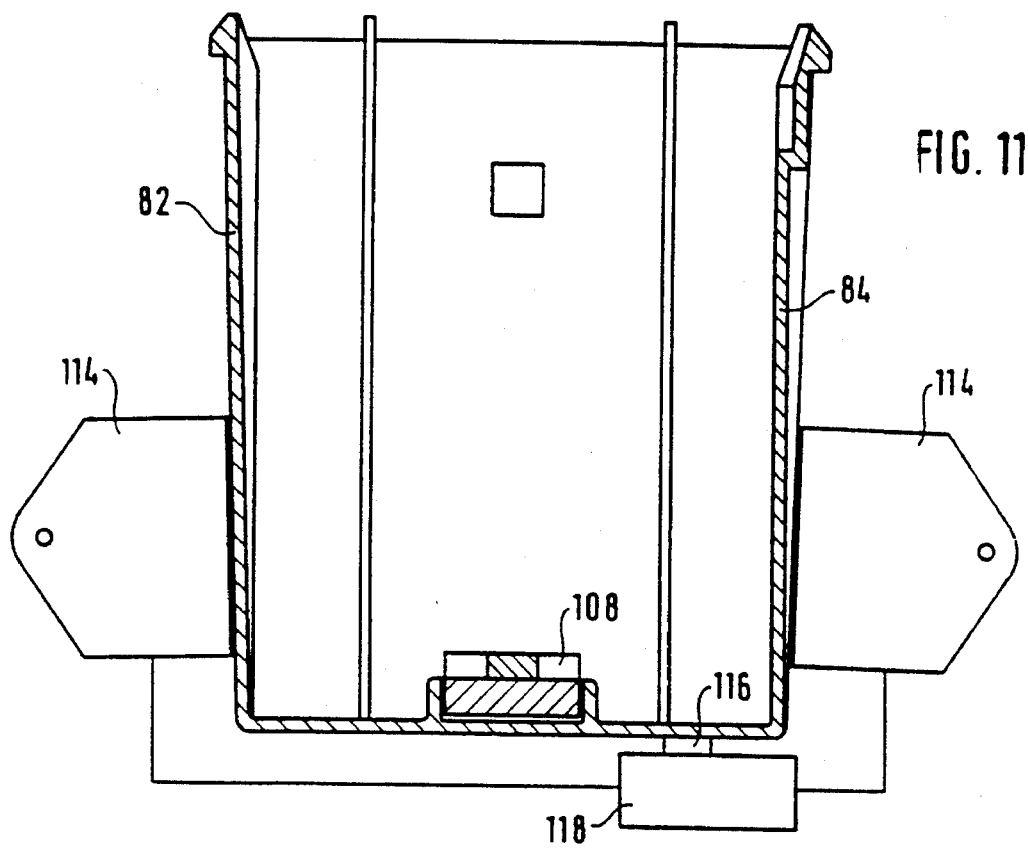
FIG. 11 is a cross sectional view of a vat with a heater.
Figure 12:
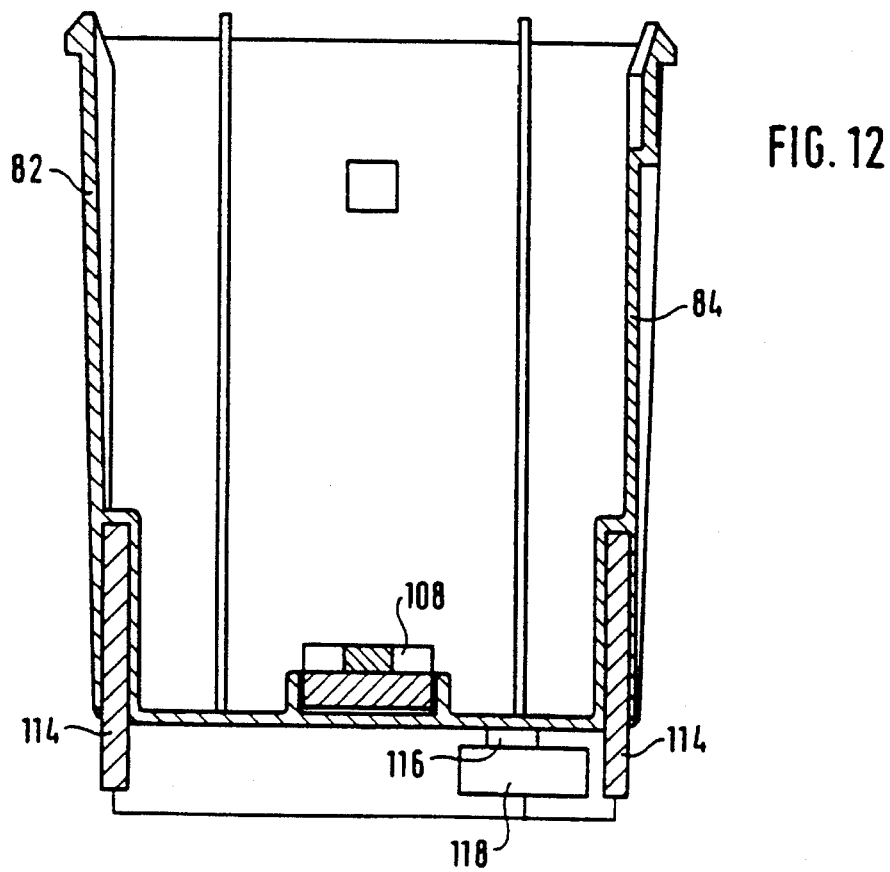
FIG. 12 is another cross sectional view of a vat with a heater.

FIGS. 11 and 12 show embodiments of heatable vats. FIG. 11 shows a cross section of a vat 48, where the heating elements 114 are arranged underneath the floors 104 and on the outside of the walls 82, 84. With this arrangement the goal of uniform thermal transmission to the vats and thus to the reagents located in said vats is achieved. The heating elements 114 can be housed stationarily in the housing 42 of the device, so that the vats 48 can also be removed without separating the electric connections. In the embodiment shown the heating elements 114 engage force-lockingly from the outside with the vats 48 and thus yield a good decoupling of the thermal energy. This embodiment has the advantage that the vats 48 can be used without any structural modifications in the same manner for heatable processing stations as for unheated ones.

In another embodiment, as shown in FIG. 12, the heating elements 114 are integrated into the floors 104 and into the walls 82, 84, 90, 92. In this case a special design of the vats 48 is necessary, but the heat transfer from the heating elements 114 to the reagents can be improved and radiation to the environment can be reduced.

In another embodiment temperature probes 116 are arranged in the floors 104 or in the walls 82, 84, 90, 92 or on the inside of the vats 48. By means of regulating circuits 118 the heating elements 114 can be controlled in such a manner that a constant temperature can be set. The temperature can be adjusted individually for each vat 48, so that the targeted processing quality and processing duration of the preparations can be optimized. This represents a significant improvement over prior art automatic dyeing machines, in which the dyeing vats can be heated by means of a common water bath and, therefore, only one uniform heating up is possible.

Regions underneath the vats 48 below the compartments 106 are recessed from heating elements and temperature probes. Thus, even for heatable vats 48 a faultless magnetic coupling between the drives 112 and the agitator blades 108 is produced.

To construct the described device, commercially available materials and components can be used, so that the fabrication and also the acquisition of individual parts is unusually good. With the device all routine dyeing methods can be conducted that are part of routine laboratory operations. In so doing, laboratory personnel avoids contact with the reagents during the dyeing operation; and a high, consistent quality is obtained with the automated processing sequence.

To implement processing measures, the procedure is as follows. Microscope slides 10 with preparations 12 are first inserted into object slide holders 14; the object slide holders 14 are then put into corresponding positions A, B, . . . of the drawer 44 and conveyed into the feed station 38 by pushing in the drawer 44. Subsequently the dyeing program desired for each position is programmed or preprogrammed and the stored dyeing program is called. At this stage the object slide holders 14 are removed in succession from the feed station 38 by means of the conveyor 18 and conveyed to the specific processing stations 16. In so doing, first the drying chamber 64, then the preprocessing and dyeing baths are traversed. Upon transport from one processing station 16 to the next, thus also when skipping several processing stations, the object slide holder 14 is guided in the middle between two rows of processing stations 16 by way of a drip area 36, in order to prevent the reagents from polluting each other by means of still adhering drops of the preceding processing station. The agitator blades 108 can be put into service in all of the preprocessing and dyeing baths, in order to circulate the fluid. Said agitator blades are driven by way of stationary drivers without making contact.

During the processing duration, the program line of the processing method is compared by the computer 28 with the program lines of the other processing methods; and the next object slide holder 14 is removed from the feed station 38, as soon as a parallel processing run is guaranteed. Thus, all of the object slide holders 14 put into the feed station 38 can be led in succession to the corresponding processing stations 16, even when the dyeing method of the first removed object slide holder has not yet finished. Following completion of the processing method, the object slide holder 14 in the removal station 40 is then put into the same position in which it was also put into the feed station 38. At this stage they can be removed by pulling out the drawer 44 for further examination.

We claim:

1. Process for simultaneously performing a plurality of programs for dyeing histological preparations arranged on microscope slides, wherein for each dyeing program a program line stored in a computer controller includes a sequence of transport times, processing times, optional processing temperatures and processing stations, and wherein slides for processing by a selected dyeing program are carried on one of a plurality of slide holders, the process comprising the steps of:

placing the slide holders in a position in a feed station;

identifying the position of each slide holder in the feed station to the computer controller;

selecting a dyeing program for each slide holder;

determining an operating sequence and a program start for a parallel run of each selected program without overlap at a processing station;

initiating each dyeing program according to the determined program start;

transporting a slide holder on a computer-controlled conveyor to one of a series of processing stations according to the selected dye program to expose the slides to a dye step at the processing station;

separating the conveyor from the slide holder after the slide holder has entered the processing station;

wherein after separating from the slide holder the conveyor is directed to transport at least one other slide holder to an unoccupied processing station according to a selected dyeing program for said other slide holder; and, wherein the steps of transporting each slide holder and separating the conveyor from the transported slide holder are repeated in accordance with the determined operating sequence so that the slide holders are transported in succession to the processing stations according to the selected dyeing program; and following completion of each dyeing program, transporting each slide holder to a removal station.

2. Process as claimed in claim 1, wherein the step of transporting a slide holder to the processing stations comprises accelerating the slide holder from a station in which the slide holder is positioned in a manner substantially to avoid imparting a swiveling motion to the slide holder, subsequently moving the slide holder at constant velocity to a next station and there decelerating the slide holder in a manner substantially to avoid imparting a swiveling motion to the slide holder.

3. Process, as claimed in claim 1, wherein the step of transporting a slide holder includes moving the slide holder continuously from a processing station over a drip area to a next processing station in accordance with the dyeing program.

4. Process, as claimed in claim 1, wherein the slide holders are placed in the removal station in a position corresponding to a position in which the slide holders were placed into the feed station.

5. Process, as claimed in claim 1 or 4, wherein the slide holders are placed from a front side of a housing enclosing the feed, removal and processing stations into the feed station and are removed from the removal station.

6. Process for simultaneously performing a plurality of programs for dyeing histological preparations arranged on microscope slides, wherein for each dyeing program a program line stored in a computer controller includes a sequence of transport times, processing times, optional processing temperatures and processing stations, and wherein slides for processing by a selected dyeing program are carried on one of a plurality of slide holders, the process comprising the steps of:

selecting a dyeing program for each slide holder:

determining an operating sequence and a program start for a parallel run of each selected program without overlap at a processing station:

initiating each dyeing program according to the determined program start;

transporting a slide holder on a computer-controlled conveyor to one of a series of processing stations according to the selected dye program to expose the slides to a dye step at the processing station;

separating the conveyor from the slide holder after the slide holder has entered the processing station;

wherein after separating from the slide holder the conveyor is directed to transport at least one other slide holder to an unoccupied processing station according to a selected dyeing program for said other slide holder;

wherein the steps of transporting each slide holder and separating the conveyor from the transported slide holder are repeated in accordance with the determined operating sequence so that the slide holders are transported in succession to the processing stations according to the selected dyeing program; and, wherein the dyeing programs and the feeding and removal of slide holders are performed in a housing having a closed top side, the process further comprising the step of drawing off reagent vapors.

7. Process, as claimed in claim 6, wherein in processing stations with liquid reagents the reagents are circulated during the processing period.

8. Process, as claimed in claim 6, wherein the dyeing programs are performed in heated processing stations.

9. Process, as claimed in claim 6, further comprising the step of heating a slide at least one of before and after individual dyeing programs are performed.

10. Device for simultaneously performing a plurality of methods for dyeing histological preparations arranged on microscope slides, said device comprising:

a plurality of slide holders;

a feed station, the feed station having a plurality of positions for the slide holders;

a plurality of processing stations;

control means, comprising a memory in which a plurality of program lines for dyeing methods is stored, each program line including transport times, processing times, processing temperatures and locations of individual processing stations, wherein, said feed station positions are identified in the memory for a dyeing program to be conducted, and a computer that calculates a program start for each selected dyeing method for a non-overlapping parallel run of the program lines;

a conveyor for individually transporting each object slide holder to the processing stations, the conveyor including coupling elements to releasably engage a slide holder so that the conveyor is available to transport another slide holder;

the conveyor being operatively connected to the control means, wherein the control means directs the conveyor to transport each slide holder in succession from the feed station to a series of processing stations according to a dyeing method selected for said each slide holder;

the control means controlling the conveyor for transport of the slide holders to the processing stations in a parallel non-overlapping processing sequence; and, a removal station in which slide holders are placed after a dyeing program is completed.

11. Device, as claimed in claim 10, wherein the removal station has a plurality of positions for inserting and depositing the slide holders; and wherein the control means controls the conveyor so that the slide holders are placed in the removal station in a position corresponding to a position from which the slide holders were removed from the feed station.

12. Device, as claimed in claim 10, wherein the control means further comprises an actuator which controls the movement of the conveyor between the individual processing stations so that a transported slide holder is accelerated first from a station in a manner substantially to avoid imparting a swiveling motion to the slide holder, subsequently moved at constant velocity, and finally decelerated at a next station in a manner substantially to avoid imparting a swiveling motion to the slide holder.

13. Device, as claimed in claim 10, further comprising a separate drip area above which the slide holders are transported without interruption between processing stations.

14. Device, as claimed in claim 13, wherein the drip area is designed as a chamber through which water flows and includes an inlet and an outlet.

15. Device, as claimed in claim 10, wherein the feed station and the removal station have a front sided access in a housing enclosing the device.

16. Device, as claimed in claim 15, wherein the feed station and the removal station include a horizontally moveable drawer; and wherein in a pushed in position Of the drawer in the housing the conveyor has access to the slide holders in the feed and removal stations and in a pulled-out position of the drawer extending from the housing the slide holders are accessible to an operator.

17. Device, as claimed in claim 16, wherein the drawer includes at least one of a bearing surface for the slide holders and a plurality of vats in which the slide holders are stored in the feed station and the removal station.

18. Device, as claimed in claim 16, wherein the drawer includes a parallel guide, which comprises two toothed racks, which engage with gear wheels, disposed on a common shaft.

19. Device, as claimed in claim 16, wherein the drawer includes a vertical outer wall, which in the pushed-in position closes an opening in the housing of the device.

20. Device, as claimed in claim 19, wherein a seal is arranged between the vertical outer wall of the drawer and a wall region adjacent to the opening in the housing.

21. Device, as claimed in claim 19, wherein the housing further comprises between the opening in the housing and an upper cover a wall region having a substantially vertical portion which together with the upper cover forms a collecting space for reagent vapors.

22. Device, as claimed in claim 21, wherein the collecting space is connected to an exhauster.

23. Device for simultaneously performing a plurality of methods for dyeing histological preparations arranged on microscope slides, said device comprising:

a plurality of slide holders;

a feed station;

a plurality of processing stations comprising vats with reagents;

a drying chamber:

control means, comprising a memory in which a plurality of program lines for dyeing methods is stored, each program line including transport times, processing times, processing temperatures and locations of individual processing stations, and a computer that calculates a program start for each selected dyeing method for a non-overlapping parallel run of the program lines; and a conveyor for individually transporting each object slide holder to the processing stations, the conveyor including coupling elements to releasably engage a slide holder so that the conveyor is available to transport another slide holder;

the conveyor being operatively connected to the control means, wherein the control means directs the conveyor to transport each slide holder in succession from the feed station to a series of processing stations according to a dyeing method selected for said each slide holder;

the control means controlling the conveyor for transport of the slide holders to the processing stations in a parallel non-overlapping processing sequence.

24. Device, as claimed in claim 23, wherein the processing stations are arranged in two parallel rows separated by a drip area between the two parallel rows the processing stations being fixed in a stationary position in the housing.

25. Device, as claimed in claim 23, wherein the vats located in the processing stations and the drying chamber each include holding elements for inserted slide holders, the holding elements comprising open blind slots in two opposite inner walls of the vats and the drying chamber, in which slots laterally protruding legs of coupling elements of the slide holders are inserted.

26. Device, as claimed in claim 25, wherein the other inner walls of the vats and the drying chamber include guide rods.

27. Device, as claimed in claim 26, wherein the guide rods are arranged in pairs on both insides of the walls.

28. Device, as claimed in claim 26, wherein the guide rods protrude beyond an upper rim of the vats and drying chamber and have inlet slopes.

29. Device, as claimed in claim 23, wherein the vats are made of non-magnetic material, and cup-shaped compartments for agitator blades are arranged in the floors of the vats.

30. Device, as claimed in claim 29, wherein armatures made of a magnetic material are integrated into the agitator blades.

31. Device, as claimed in claim 30, further comprising agitator drives that are magnetically coupled to the armatures of the agitator blades and are positioned below the vats in the processing stations.

32. Device, as claimed in claim 23, further comprising means for heating at least one processing station.

33. Device, as claimed in claim 32, wherein processing stations having heating means are arranged side-by-side.

34. Device, as claimed in claim 32, wherein the means for heating the processing stations include heating elements positioned in a housing below processing station vats and coupled thermally to the vats.

35. Device, as claimed in claim 32, wherein the heating elements are attached to the vats.

36. Device, as claimed in claim 35, wherein the heating elements are positioned on at least one of an underside of vat floors and outsides of the vat walls.

37. Device, as claimed in claim 36, wherein the heating elements are integrated into at least one of the floors and the walls.

38. Device, as claimed in claim 34 further comprising temperature probes and regulating circuits connected to the temperature probes (116) and the heating elements, the temperature probes being thermally coupled to one of the floors and the walls of the vats.

39. Device, as claimed in claim 38, wherein the housing underneath the vats is spaced from the heating elements and the temperature probes.

40. Device, as claimed in claim 23, wherein the conveyor further comprises a first carriage for movement in a transverse direction and a parallel drive; and a second carriage for movement in a longitudinal direction on the first carriage, and a lifting and lowering device mounted on the second carriage.

41. Device, as claimed in claim 40, wherein the lifting and lowering device includes a parallel guide, which comprises two guide rods to support the coupling elements.

42. Device, as claimed in claim 41, wherein each coupling element comprises a bearing plate and two parallel gripper hooks that are mounted spaced apart on the bearing plate.

* * * * *